United States Patent

Vorbrueggen et al.

Patent Number: 4,960,907
Date of Patent: Oct. 2, 1990

[54] PROCESS FOR THE PRODUCTION OF BICYCLO(3.3.0)OCTANE-3,7-DIONE-2-CARBOXYLIC ACID ESTERS

[75] Inventors: Helmut Vorbrueggen; Konrad Krolikiewicz, both of Berlin, Fed. Rep. of Germany

[73] Assignee: Schering Aktiengesellschaft, Berlin and Bergkamen, Fed. Rep. of Germany

[21] Appl. No.: 391,618
[22] PCT Filed: Jan. 7, 1988
[86] PCT No.: PCT/DE88/00011
§ 371 Date: Jul. 24, 1989
§ 102(e) Date: Jul. 24, 1989
[87] PCT Pub. No.: WO88/05429
PCT Pub. Date: Jul. 28, 1988

[30] Foreign Application Priority Data

Jan. 23, 1987 [DE] Fed. Rep. of Germany ....... 3702385

[51] Int. Cl.$^5$ ............... C07D 317/72; C07D 319/08; C07C 69/74; C07C 67/32
[52] U.S. Cl. ...................................... 549/336; 560/119
[58] Field of Search ......................... 560/119; 549/336

[56] References Cited

OTHER PUBLICATIONS

Weiss et al., J. Org. Chem., 42, 3089 (1977).
Barco et al., Ibid., 45, 4776 (1980).

Primary Examiner—Nicky Chan
Attorney, Agent, or Firm—Millen, White & Zelano

[57] ABSTRACT

The invention relates to a process for the production of D,L-bicyclo[3.3.0]octane-3,7-dione-2-carboxylic acid esters of Formula I

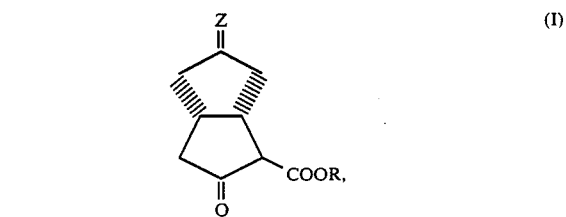

wherein
R is methyl or ethyl, and
Z is oxygen or the ketal residue

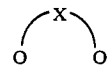

wherein X means ethylene, trimethylene or 2,2-dimethyltrimethylene, characterized in that D,L-bicyclo[3.3.0]octane-3,7-dione-2,6-dicarboxylic acid esters of Formula II

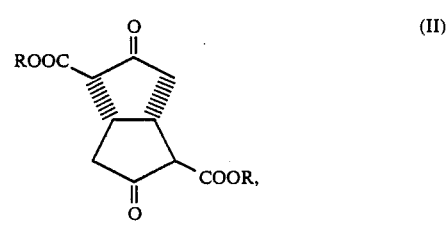

wherein R has the meanings given above, are partially saponified and decarboxylated in an aqueous or water-containing medium in the presence of acids, and are optionally selectively ketalized.

4 Claims, No Drawings

PROCESS FOR THE PRODUCTION OF BICYCLO(3.3.0)OCTANE-3,7-DIONE-2-CARBOXYLIC ACID ESTERS

The invention relates to a process for the preparation of bicyclo[3.3.0]octane-3,7-dione-2-carboxylic acid esters and associated monoketals.

Bicyclo[3.3.0]octane-3,7-dione-2-carboxylic acid esters are important potential intermediates for the production of carbacyclin derivatives and sesquiterpenes, heretofore obtainable only with difficulties.

The cleavage of D,L-bicyclo[3.3.0]octane-3,7-dione-2,6-dicarboxylic acid diesters of Formula II

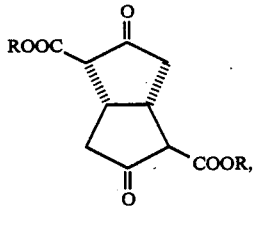
(II)

$R = CH_3, C_2H_5$ with sodium methylate in DMSO-methanol [according to U. Weiss et al., J. Org. Chem. 42 : 3089 (1977)] yields merely traces of D,L-bicyclo[3.3.0]octane-3,7-dione-2-carboxylic acid esters.

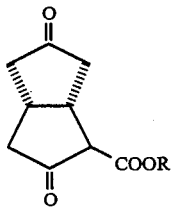

$R = CH_3, C_2H_5$

It has now been discovered surprisingly that D,L-bicyclo[3.3.0]octane-3,7-dione-2-carboxylic acid esters can be produced in yields of 50–70% by partially saponifying and decarboxylating D,L-bicyclo[3.3.0]octane-3,7-dione-2,6-dicarboxylic acid esters of Formula II in an aqueous or water-containing medium in the presence of acids.

Therefore, the invention relates to the selective cleavage of the D,L-diesters II under gentle acidic conditions to D,L-bicyclo[3.3.0]octane-3,7-dione-2-carboxylic acid esters.

The process for the production of D,L-bicyclo[3.3.0]octane-3,7-dione-2-carboxylic acid esters of Formula I

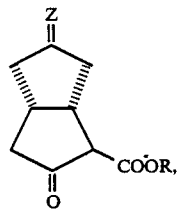
(I)

wherein

R is methyl or ethyl, and
Z is oxygen or the ketal residue

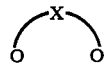

wherein X means ethylene, trimethylene or 2,2-dimethyltrimethylene,
is characterized in that D,L-bicyclo[3.3.0]octane-3,7-dione-2,6-dicarboxylic acid esters of Formula II

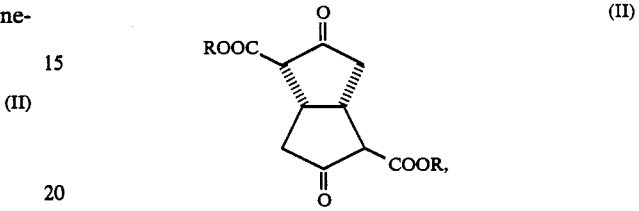
(II)

wherein R has the meanings given above,
are partially saponified and decarboxylated in an aqueous or water-containing medium in the presence of acids, and are optionally selectively ketalized.

The starting compounds of Formula II are very readily obtainable by alkaline treatment of the bicyclo[3.3.0]octane-3,7-dione-2,4,6,8-tetracarboxylic acid esters III [cf. J. Org. Chem. 42 : 3089 (1977); Org. Synth. 64 : 27–37 (1985)].

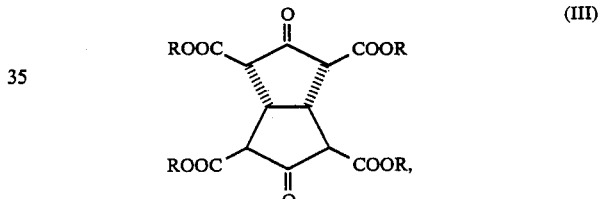
(III)

The acidic cleavage of the D,L-diesters of Formula II to the D,L-monoesters of Formula I is preferably performed in $H_2O$ with water-soluble acids or acid mixtures which are to be maximally insoluble in methylene chloride, in amounts of 0.05–1 mole at a pH of 1–6, preferably 3–4, and at temperatures of 20°–150° C., preferably at 80°–100° C. During subsequent cooling to 2° C., the unreacted D,L-diester II is crystallized and is thus to the largest part separated and recovered. Extraction of the filtrate with methylene chloride then results in a crude product from which pure D,L-monomethyl ester of Formula I (R=$CH_3$, Z=O) is crystallized.

While the tetracarboxylic acid ethyl ester III (R=$C_2H_5$), mp 107° C., as well as the D,L-dicarboxylic acid ethyl ester II (R=$C_2H_5$), mp 102.7° C., are crystalline, the D,L-diketone monoethyl ester I (R=$C_2H_5$) is oily, so that this compound can be obtained in the pure form only by chromatography, and therefore has a lesser importance as an intermediate as compared with the crystalline D,L-diketone monomethyl ester (R=$CH_3$).

Suitable water-soluble acids for splitting off the ester group are citric acid, lactic acid, oxalic acid, acetic acid, formic acid, aspartic acid, glutamic acid, $NaH_2PO_4$, amidosulfonic acid, etc., preferably citric acid. When using formic acid and acetic acid, added in relatively large amounts as the solvents, these acids can be very easily removed by evaporating under vacuum.

In order to shorten the reaction period, the process should, if at all possible, be conducted at temperatures of 50°–90° C.

Since the β-keto ester systems in the D,L-diester II are weak acids (inherent acidity), II can be converted into I in water or in azeotropic mixtures with organic solvents even without the addition of carboxylic acids, but in this case at a reduced reaction rate. Thus, II (R=CH$_3$) yields I (R=CH$_3$), by boiling for 1.5 hours in xylene-H$_2$O at 120°–140° C., in an amount of about 41%.

The D,L-monoesters I (Z=O) can be selectively converted into the D,L-monoketals I

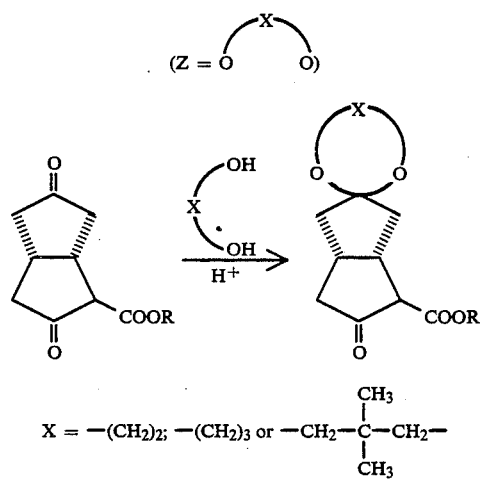

$$X = -(CH_2)_2; \ -(CH_2)_3 \text{ or } -CH_2-\underset{\underset{CH_3}{|}}{\overset{\overset{CH_3}{|}}{C}}-CH_2-$$

These monoketals are excellent starting materials for the production of carbacyclins and have heretofore been prepared in accordance with K. C. Nicolaou et al., J. Chem. Comm. 433 (1979) by carboethoxylation of the monoketals of bicyclo[3.3.0]-octane-3,7-dione.

EXAMPLE 1

Production of
D,L-Bicyclo[3.3.0]octane-3,7-dione-2-carboxylic Acid Methyl Ester I (R=CH$_3$) from
D,L-Bicyclo[3.3.0]octane-3,7-dione-2,6-dicarboxylic Acid Dimethyl Ester II (R=CH$_3$)

(a) With Citric Acid 105 g (0.5 mole) of citric acid monohydrate is dissolved in 1.3 l of distilled H$_2$O and heated in an oil bath to 85°–90° C. (internal temperature). The finely pulverized dimethyl ester (127 g=0.5 mol) is added all at once, and the resultant suspension is vigorously stirred, a clear solution being formed within 30 minutes. After another 90 minutes at 85°–90° C. internal temperature in the flask, the mixture is cooled off as quickly as possible with ice water to 2° C. internal temperature in the flask; during this step, unreacted diester II is crystallized as a colorless compound. After about 30 minutes at 2° C., the mixture is filtered and rinsed with 500 ml of ice water, thus recovering, after drying at 40–50° C. in a vacuum drying cabinet,33.6 g (mp 103° C.)=26.3% of the utilized amount of pure diester II.

In case this reaction is conducted with larger amounts of II and thus in larger volumes of aqueous citric acid, and this solution, for technical reasons, can be cooled only relatively slowly to 2° C., then the reaction period must be shortened from 120 minutes at 85°–90° C. to 60–90 minutes, since the ester cleavage proceeds still further during more gradual cooling.

The ice-cold filtrate is extracted with 3×300 ml of CH$_2$Cl$_2$, dried (Na$_2$SO$_4$), and concentrated. The residue (68 g) is dissolved in 250 ml of boiling methyl tert-butyl ether and slowly cooled to 24° C.; during this step, 28 g of practically pure diketone monomethyl ester I (mp 67° C.) is crystallized. (TLC shows then only traces of diester.) After evaporation of the solvent, the residue is dissolved in 150 ml of ice-cold 2 NaOH, during which step the solution must become strongly alkaline (pH=13). After extraction with 3×250 ml of CH$_2$Cl$_2$ and drying of the extracts (Na$_2$SO$_4$), about 10.4 g (15%) of diketone IV is obtained during evaporation (based on the diester II employed).

The alkaline solution is acidified to pH 3 with saturated aqueous citric acid and extracted with 3×300 ml of CH$_2$Cl$_2$. After drying (Na$_2$SO$_4$) and evaporation, 29 g of a yellow oily residue is obtained. The residue is dissolved in CH$_2$Cl$_2$ (50 ml) and filtered over a short column of nonferrous silica gel (0.063–0.2 mm) and rinsed with, in total, 1,000 ml of CH$_2$Cl$_2$ Evaporation of the filtrate yields 26.5 g of a residue yielding, after crystallization from 150 ml of methyl tert-butyl ether, 16.5 g of diketone monoester I. The mother liquor is dissolved, after evaporation, in 30 ml of toluene and chromatographed on 100 g of nonferrous silica gel (0.063–0.2 mm).

| Fractions 1 + 2 | respectively 250 ml of toluene |
| --- | --- |
| Fraction 3 | 250 ml of toluene/ethyl acetate 95:5, 2.4 g of diester II |
| Fractions 4–8 | respectively 250 ml of toluene/ethyl acetate 95:5, 5.9 g of diketone monoester I |
| Fractions 9–12 | respectively 250 ml of toluene/ethyl acetate 95:5, 1.4 g of diketone IV |

Crystallization of fractions 4–8 from 20 ml of methyl tert-butyl ether yields 5.1 g of diketone monoester I.

Total yield of diketone monoester I: 49.6 g=50% based on diester II utilized; 70.5% based on reacted diester II.

(b) With Formic Acid 2.54 g (0.01 mol) of finely pulverized dimethyl ester II is stirred in a mixture of 3 ml of 98–100% formic acid and 7 ml of H$_2$O at an internal temperature of 76° C. for 4.5 hours; during this step, II is dissolved. After heating for about 4 hours, the mixture is cooled to 22° C. and finally for 30 minutes to 2° C., and the thus-crystallized diester II (0.46 g=16.9%, mp 108° C.) is filtered off. The filtrate is evaporated twice at 40° C. under vacuum with respectively 5 ml of H$_2$O, and the residue is crystallized from 6 ml of methyl tert-butyl ether, thus obtaining in two portions about 0.64 g of I, mp 66° C. (32% based on II utilized, 39.3% based on reacted II). The mother liquors contain still more monoester according to TLC analysis.

(c) With Acetic Acid 2.54 g (0.01 mol) of finely pulverized dimethyl ester II was heated for 4.5 hours in a mixture of 3 ml of acetic acid and 7 ml of H$_2$O. After cooling overnight to 22° C. and further cooling for one hour to 2° C., 0.68 g (26.77%) of II, mp 108° C., was filtered off and evaporated twice after addition of respectively 5 ml of H$_2$O. The colorless residue (1.3 g) yielded, upon crystallization from 4 ml of methyl tert-butyl ether, 0.58 g of III, mp 66.4° C. (26.9% based on II utilized, 40% based on reacted II).

(d) In Xylene-H₂O 2.54 g (0.01 mol) of finely pulverized diester II (R=CH₃) was refluxed in 30 ml of xylene and 10 ml of H₂O at an oil bath temperature of 160° C. for 1.5 hours, the temperature in the flask rising gradually from 120° C. to 140° C.

After removal of the xylene by vacuum distillation at 35° C., the residue (2.7 g) was dissolved in 15 ml of toluene and chromatographed on a column with 80 g of nonferrous silica gel. After a forerunning with 500 ml of toluene, 300 ml of toluene-ethyl acetate mixture (98:2) eluted 0.280 g (11%) of crystalline diketone dimethyl ester II (R=CH₃). Further elution with 300 ml of toluene-ethyl acetate mixture (95:5) resulted in 0.80 g (40.8%) of crystalline diketone monomethyl ester I (R=CH₃). Elution with 300 ml of ethyl acetate-toluene finally yielded 0.6 g (43%) of diketone IV.

(e) In H₂O

The reaction of pure diester II (R=CH₃) in H₂O at 85°–90° C. takes place analogously to 1(d), but requires about 5–6 hours in order to lead to the analogous yield of monoester I (R=CH₃).

EXAMPLE 2

Preparation of the Neopentyl Ketal of Bicyclo[3.3.0]-octane-3,7-dione-2-carboxylic Acid Methyl Ester I (R=CH₃; Z=—O—CH₂—C(CH₃)₂—CH₂—O—)

1.0 g (5.01 millimoles) of D,L-bicyclo[3.3.0]-octane-3,7-dione carboxylic acid methyl ester is stirred with 783 mg (7.52 mmol) of neopentyl glycol (MERCK AG) and 58 mg (0.25 mmol) of DL-camphorsulfonic acid (Fluka) and 1.0 g of anhydrous MgSO₄ (MERCK AG) in 8 ml of CH₂Cl₂ for 4 hours at 22°–24° C., whereupon a TLC sample in the system of hexane-diethyl ether (4–6) indicates, besides traces of starting material, as the primary main product the formation of the desired D,L-monoketal, as well as small amounts of the diketal. After the reaction mixture has been worked up with saturated NaHCO₃ solution, the combined CH₂Cl₂ solution is dried (MgSO₄) and evaporated. The residue (1.46 g) is filtered over a column of 10 g of nonferrous silica gel in hexane-ether (8:2). After evaporation, the filtrate is crystallized (1.21 g) from about 4 ml of hot hexane. After standing overnight at 24° C., 1.08 g (75%) of pure D,L-monoketal, mp 68°–70° C., is obtained. After the filtrate has been removed by evaporation, the diketal has markedly accumulated in the residue (0.080 g).

REFERENCE EXAMPLE

Preparation of D,L-Bicyclo[3.3.0]octane-3,7-dione2,6-dicarboxylic Acid Dimethyl Ester II An ice-cold solution of 80 g (2 mol) of NaOH in 1.5 l of methanol is combined dropwise under cooling with 348.3 g (2 mol) of acetonedicarboxylic acid methyl ester within 30 minutes, a yellow precipitate being obtained. The methanol solution is thereafter heated to boiling under agitation, the precipitate being dissolved during this step. During one hour, 164.2 g (1.13 mol) of a 40% solution of glyoxal in H₂O is added dropwise to the hot solution, the reaction mixture continuing to boil. Subsequently, the mixture is allowed to cool down to room temperature and is finally cooled to 4° C. After one hour at 4° C., the mixture is filtered off and the salt washed with, in total, 600 ml of methanol until the filtrate becomes colorless. The yellowish disodium salt of the tetraester III is suspended in 2 l of H₂O and a solution of 120 g (3 mol) of NaOH in 500 ml of H₂O is added. After about 18 hours at 22° C., the clear solution is acidified in increments with 195 g of citric acid monohydrate under evolution of CO₂ until a pH of about 8.5 is obtained; the diester II begins to crystallize during this step. After cooling and allowing the mixture to stand for one hour at 3° C., the diester II is filtered off, washed with 500 ml of H₂O, and dried under vacuum at 40° C. Yield: 154 g (60.4% based on acetonedicarboxylic acid dimethyl ester).

We claim:

1. A process for the production of D-Lbicyclo[3.3.-0]octane-3,7-dione-2-carboxylic acid esters of Formula I

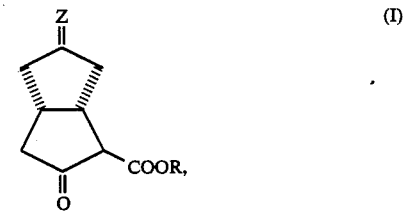

wherein
R is methyl or ethyl, and
Z is oxygen or the ketal residue

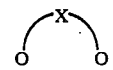

wherein X means ethylene, trimethylene or 2,2-dimethyltrimethylene,
characterized in that D,L-bicyclo[3.3.0]octane-3,7-dione-2,6-dicarboxylic acid esters of Formula II

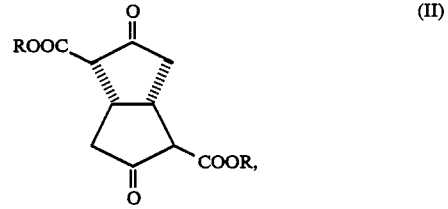

wherein R has the meanings given above,
are partially saponified and decarboxylated in an aqueous or water-containing medium in the presence of acids, and are optionally selectively ketalized.

2. A process according to claim 1, characterized by utilizing as the acids water-soluble, volatile acids or water-soluble, nonvolatile acids insoluble in methylene chloride.

3. A process according to claim 2, characterized by utilizing formic acid or acetic acid as the volatile acids.

4. A process according to claim 2, characterized by utilizing citric acid or glutamic acid as nonvolatile acids.

* * * * *